United States Patent [19]

Riediker et al.

[11] Patent Number: 4,910,121
[45] Date of Patent: Mar. 20, 1990

[54] PHOTOPOLYMERIZABLE COMPOSITION CONTAINING METALLOCENES

[75] Inventors: Martin Riediker, Riehen; Martin Roth, Giffers; Niklaus Bühler, Marly; Joseph Berger, Basel, all of Switzerland

[73] Assignee: Ciba-Geigy Corporation, Ardsley, N.Y.

[21] Appl. No.: 80,241

[22] Filed: Jul. 28, 1987

Related U.S. Application Data

[60] Continuation of Ser. No. 827,046, Feb. 7, 1986, abandoned, which is a division of Ser. No. 576,518, Feb. 2, 1984, Pat. No. 4,590,287.

[30] Foreign Application Priority Data

Feb. 11, 1983 [CH] Switzerland .............. 784/83

[51] Int. Cl.$^4$ .............................. G03C 1/68
[52] U.S. Cl. .................... 430/281; 430/286; 430/287; 430/288; 430/916; 430/919; 430/920; 430/921; 430/922; 522/31; 522/55; 522/63; 522/65; 522/66; 522/89; 522/121; 522/158; 522/142; 260/428; 544/64; 544/225; 544/164; 544/165
[58] Field of Search .............. 260/428 CY, 429 Y; 544/64, 225; 546/11; 548/101; 556/53; 430/218, 286, 287, 288, 916, 919, 920, 921, 922; 522/31, 55, 63, 65

[56] References Cited

U.S. PATENT DOCUMENTS

| | | | |
|---|---|---|---|
| 3,032,569 | 5/1962 | Freeman, Jr. et al. | 260/419 CY |
| 3,071,605 | 1/1963 | Morehouse | 260/429 CY |
| 3,505,369 | 4/1970 | Deffner | 260/429 CY |
| 3,678,088 | 7/1972 | Hedberg et al. | 260/429 CY |
| 4,548,891 | 10/1985 | Riediker et al. | |

FOREIGN PATENT DOCUMENTS 2753889  6/1978  Fed. Rep. of Germany.

OTHER PUBLICATIONS

Chemical Abstracts 95 23650n (1981).
Journal of Organometallic Chemistry 2, 206–212 (1964).
Chem. Abstract, vol. 85, 21953h, (1976).
Inorganica Chimica Acta, 52, 197–204 (1981).
Journal of Organic Chemistry 4, 446–454 (1965).
K. Kaeriyama et al., J. Polymer Sci., Poly Chem Ed, 10, 2833 (1972).
S. C. Cohen et al., J. Organometal. Chem., 10, 471 (1967).
E. Samuel et al., J. Amer. Chem. Soc. 95, 6263 (1973).
J. C. Leblanc et al., Org. Magn. Resonance 14, 157 (1980).

Primary Examiner—Jack P. Brammer
Attorney, Agent, or Firm—Luther A. R. Hall

[57] ABSTRACT

Titanocenes containing $\pi$-cyclopentadienyl ligands, in which one or two carbocyclic or heterocyclic aromatic rings are attached to the metal atom, said aromatic rings being substituted by fluorine in at least one of the two ortho-positions relative to the metal-carbon bonds, are suitable photoinitiators for the photopolymerization of ethylenically unsaturated substrates. They are distinguished by high sensitivity, stability to air and heat, and are very effective in the range from UV light to visible light.

6 Claims, No Drawings

PHOTOPOLYMERIZABLE COMPOSITION CONTAINING METALLOCENES

This is a continuation of application Ser. No. 827,046, filed on Feb. 7, 1986, now abandoned, which in turn is a divisional of application Ser. No. 576,518, filed on Feb. 2, 1984, now U.S. Pat. No. 4,590,287, issued on May 20, 1986.

The present invention relates to metallocenes which contain at least partially fluorinated aromatic radicals, to a photopolymerisable composition of ethylenically unsaturated compounds which contain these metallocenes as photoinitiators, to a substrate coated with said composition, and to a process for the production of photographic relief images which comprises the use of the coated substrate.

Photolithography has made an appreciable contribution to the development of electronics. To transmit images, substances which are sensitive to radiation and which are applied to a substrate are exposed to form an image, whereby the solubility of the exposed areas so changes that either the exposed areas (positive process) or the unexposed areas (negative process) can be removed with a suitable solvent. The substrates can accordingly be modified to produce e.g. printed or integrated circuits in known manner.

There are various light-sensitive substances which are employed in this resist method and are often adjusted for specific techniques. A group of suitable photoresists comprises compounds having ethylenically unsaturated double bonds and which are photopolymerised by suitable photoinitiators under irradiation.

Most of the known initiators are effective in the wavelength range of UV light up to about 420 nm. By means of spectral sensitization it is possible to extend the range of sensitivity in the visible range of light up to about 600 nm. It is thus possible to use e.g. argon or crypton lasers for the linear imaging.

The initiator systems used in practice up to now have the drawback of insufficient sensitivity and/or storage stability, thus necessitating the use of high power lasers - where lasers are used - which are expensive and have a short life.

Combinations of organic dyes and amines as photoinitiators for acrylates and methacrylates have been proposed in DE-OS 2,753,889. However, their sensitivity is too low for economic use.

It has also long been known to use dicyclopentadienyltitanocenes as photoinitiators for irradiating ethylenically unsaturated compounds with visible light (q.v. for example J. of Polymer Science 10 (1972), pp. 2833 to 2840, and Inorganica Chimica Acta 52 (1981), pp. 197-204). The initiators employed, viz. dicyclopentadienyldichlorotitanocene and dicyclopentandienyldiphenyltitanocene, are thermally unstable compounds. Although dicyclopentadienyldichlorotitanocene is stable in air, it is insufficiently light-sensitivie. On the other hand, dicyclopentadienyldiphenyltitanocene is very unstable in air but sufficiently light-sensitive. These compounds are unsuitable for use in practice.

Photoinitiators for photopolymerisation which are sufficiently stable in air and restistant to light and heat and therefore also storage stable, which are are effective in the range from UV light to visible light, especially in the range of 500 nm, even in thick layers, and which have high sensitivity, are not yet known in the art. It would be highly desirable if such initiators were available in order also to be able to use relatively low power lasers for imaging by photopolymerisation, in addition to the conventional imaging methods.

Accordingly, it is the object of the present invention to provide such photoinitiators and photopolymerisable compositions which contain them.

The present invention therefore relates to titanocenes of the formula I

wherein
M is the tetravalent titanium atom,
$R^1$ is each independently unsubstituted or substituted cyclopentadienyl$\ominus$, indenyl$\ominus$ or both symbols $R^1$ together denote an unsubstituted or substituted radical of the formula II

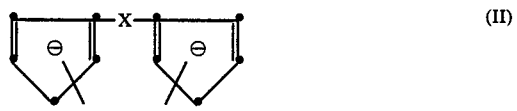

wherein X is $(CH_2)_n$, in which n is 1, 2 or 3, $C_2$–$C_{12}$alkylidene, cycloalkylidene containing 5 to 7 ring carbon atoms, $SiR_2^4$ or $SnR_2^4$, in which $R^4$ is $C_1$–$C_{12}$alkyl, $C_5$–$C_{12}$cycloalkyl, $C_6$–$C_{16}$aryl or $C_7$–$C_{16}$aralkyl,
$R^2$ is a 6-membered carbocyclic or 5- or 6-membered heterocyclic aromatic ring which is substituted by fluorine atoms in at least one of the two ortho-positions relative to the metal carbon bond and which may contain further substituents, or $R^2$ and $R^3$ together are a radical of the formula III

 (III)

wherein Q is a carbocyclic or heterocyclic 5- or 6-membered aromatic ring, and each of the two bonds is in the orthoposition to the Y group and each meta-position to the Y group is substituted by a fluorine atom, and Q may contain further substituents, and Y is $CH_2$, $C_2$–$C_{12}$alkylidene, cycloalkylidene containing 5 to 7 ring carbon atoms, a direct bond, $NR^4$, O, S, SO, $SO_2$, CO, $SiR_2^4$ or $SnR_2^4$,
$R^3$ is alkynyl, substituted or unsubstituted phenylalkynyl, $N_3$, CN, $SiR_3^4$ or $SnR_3^4$ or has the meaning of $R^2$, with the proviso that, if both symbols $R^1$ are unsubstituted cyclopentadienyl$\ominus$, only one of $R^2$ and $R^3$ is pentafluorophenyl.

The $R^1$ groups are preferably identical. Suitable substituents for $R^1$ are: linear or branched alkyl, alkoxy and alkenyl of preferably 1 to 18, especially 1 to 12 and most preferably 1 to 6, carbon atoms, e.g. methyl, ethyl, propyl, isopropyl, n-butyl, tert-butyl, pentyl, hexyl, octyl, decyl, dodecyl, tetradecyl, hexadecyl, octadecyl and corresponding alkenyl and alkoxy groups; cycloalkyl and cycloalkenyl containing preferably 5 to 8 ring carbon atoms, e.g. cyclopentyl, cyclohexyl, cycloheptyl, methylpentyl and methylcyclohexyl; aryl of preferably 6 to 16 carbon atoms and aralkyl of preferably 7 to 16 carbon atoms, e.g. phenyl, naphthyl, pyridinyl, benzyl and phenylethyl; nitrilo, halogen, preferably F, Cl and Br, and also amino, preferably tertiary amino which may contain linear or branched alkyl groups of 1 to 12, preferably 1 to 6, carbon atoms, in particular methyl or ethyl, or phenyl and benzyl, which amino groups can also be quaternised, in particular with linear or branched alkyl halides containing preferably 1 to 12 carbon atoms, preferably methyl or ethyl halides; linear or branched aminoalkyl, preferably tertiary aminoalkyl which may also be quaternised, in particular with alkyl halides, and the alkylene group in the aminoalkyl can be linear or branched and contains preferably 1 to 12, most preferably 1 to 6, carbon atoms, and is most preferably methylene which can be substituted by $C_1$-$C_{12}$alkyl.

The radicals $R^1$ may contain up to 3 substituents, but preferably contain one substituent. It is preferred that both substituents $R^1$ are cyclopentadienyl$^\ominus$ or methylcyclopentadienyl$^\ominus$.

X in formula II as alkylidene preferably contains 2 to 6 carbon atoms. Exemplary of alkylidene and cycloalkylidene are ethylidene, propylidene, butylidene, hexylidene, phenylmethylene, diphenylmethylene, cyclopentylidene and cyclohexylidene. $R^4$ as alkyl in the group X preferably contains 1 to 6 carbon atoms, e.g. methyl, ethyl, propyl, butyl or hexyl; and as cycloalkyl is preferably cyclopentyl or cyclohexyl; and as aryl is preferably phenyl; and as aralkyl is preferably benzyl. Most preferably X is methylene.

$R^2$ as 6-membered carbocyclic aromatic and fluorine-substituted ring may be indene, indane, fluorene, naphthalene and preferably phenyl. Preferably both ortho-positions are substituted by fluorine. Examples are: 4,6-difluoroinden-5-yl, 5,7-difluorind-6-yl, 2,4-difluorofluoren-3-yl, 1,3-difluoronaphth-2-yl and, preferably, 2,6-difluorophen-1-yl.

$R^2$ as heterocyclic aromatic 5-membered ring preferably contains one hetero-atom and, as 6-membered ring, preferably 1 or 2 hetero-atoms. Examples of such rings substituted by two fluorine atoms are: 2,4-difluoropyrr-3-yl, 2,4-difluorofur-3-yl, 2,4-difluorothiophen-3-yl, 2,4-difluoropyrid-3-yl, 3,5-difluoropyrid-4-yl and 4,6-difluoropyrimid-5-yl.

$R^2$ and $R^3$ together as radical of the formula III may be e.g.:

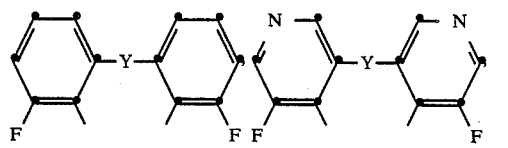

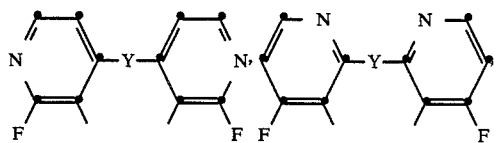

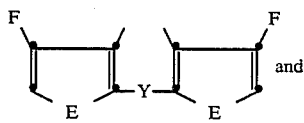 and

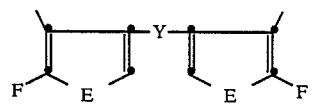

wherein E is O, S or NH. Y in formula III and in the above formulae is preferably methylene, ethylidene, propylidene, a direct bond, S or O.

The radicals $R^2$ can be partly or completely substituted by further groups. Suitable groups are: linear or branched alkyl or alkoxy, each of 1 to 18, preferably 1 to 6, carbon atoms, e.g. methyl, ethyl, propyl, butyl, pentyl, hexyl, and the corresponding alkoxy groups, with methyl and methoxy being preferred;

cycloalkyl containing preferably 5 or 6 ring carbon atoms, aryl of preferably 6 to 16 carbon atoms and aralkyl of preferably 7 to 16 carbon atoms, e.g. cyclopentyl, cyclohexyl, phenyl or benzyl; hydroxyl, carboxyl, CN, halogen such as F, Cl or Br, and amino, preferably tertiary amino which may be quaternised with an alkyl halide such as methyl chloride, methyl bromide or methyl iodide, examples of amino groups being methylamino, ethylamino, dimethylamino, diethylamino, pyrrolidyl, piperidyl, piperazyl, morphylyl, N-methylpiperazyl;

alkoxycarbonyl containing preferably 1 to 18, most preferably 1 to 6, carbon atoms in the alkoxy moiety, aminocarbonyl containing one or two $C_1$-$C_{12}$alkyl groups in the amino group, or aminocarbonyl containing heterocyclic amines such as pyrrolidine, piperidine, piperazine, N-methylpiperazine, and morpholine;

aminoalkyl, especially aminoalkyl which preferably contains $C_1$-$C_6$alkyl groups and which may be quaternised with an alkyl halide, most preferably tertiary aminoalkyl which may be substituted by $C_1$-$C_{12}$alkyl, e.g. dimethylaminomethyl and trimethylammoniummethyl iodide.

Examples of substituents for $R^3$ as phenylalkynyl are halogen such as F, Cl, Br, tertiary amino, $C_1$-$C_6$alkyl and $C_1$-$C_6$alkoxy, carboxyl, OH and CN. $R^3$ preferably has the meaning of $R^2$.

In a preferred embodiment of the invention, $R^2$ in formula I is unsubstituted or substituted 2,6-difluorophen-1-yl, or $R^2$ and $R^3$ together are an unsubstituted or substituted radical of the formula

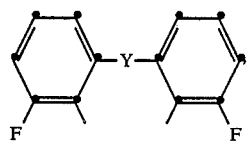

wherein Y has the meaning assigned to it above. In particular, $R^2$ and $R^3$ are 2,6-difluorophen-1-yl which contains 1 to 3 further substituents.

A preferred group of metallocenes of the formula I comprises those wherein each $R^1$ is cyclopentadienyl$^\ominus$ or $C_1$-$C_4$alkyl-substituted cyclopentadienyl$^\ominus$, and $R^2$ and $R^3$ are a radical of the formula

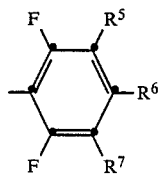

wherein each of $R^5$, $R^6$ and $R^7$ independently is a hydrogen atom, F, Cl, Br, a tertiary amino group, a quaternary ammonium group, a tertiary aminoalkyl group or a quaternary ammoniumalkyl group, with the proviso that only two of $R^5$, $R^6$ and $R^7$ are fluorine. The aminoalkyl and ammoniumalkyl groups are preferably in the paraposition to the free bond. A preferred subgroup of metallocenes of the formula I comprises those in which $R^6$ is fluorine, $R^5$ is H, F, Cl or Br and $R^7$ is H, Cl or Br, or in which $R^5$ and $R^7$ are H, fluorine, chlorine or bromine, and $R^6$ is H, Cl, Br, a tertiary amino or aminomethyl group or a quaternary ammonium or ammoniummethyl group.

The metallocenes of the formula I are prepared by known methods or by methods analogous to known ones by reacting 1 mole of a compound of the formula IV

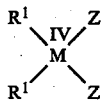    (IV)

wherein $R^1$ and $M^{IV}$ are as defined in claim 1 and Z is halogen, preferably chlorine, either with 1 mole of $LiR^2$ or $LiR^3$ and then with 1 mole of $LiR^3$ or $LiR^2$, or with 2 moles of $LiR^2$, where $R^2$ is as defined in claim 1 and $R^3$ is alkynyl, unsubstituted or substituted phenylalkynyl, $N_3$, CN, $SiR_3^4$ or $SnR_3^4$, and subsequently isolating the compounds of the formula I in a manner known per se.

The known methods are described e.g. in J. Organometal. Chem., 2 (1964), 202–212, and J. Organometal. Chem., (1965), 446–445.

The starting compounds of the formula IV, in which Z is preferably chlorine, are known. The lithium compounds, $LiR^2$ and $Li^3$, are also known or can be prepared by analogous methods by reacting $R^2$- or $R^3$-halides, especially the bromides, with butyllithium. Derivatives substituted by tertiary aminomethyl groups are obtained e.g. by reacting corresponding difluorodibromophenyl compounds, which have first been converted into lithium difluorobromophenyl compounds, with N,N-dialkylmethyleneammonium chloride, and then reacting the resultant dialkylaminomethyldifluorobromophenyl with butyllithium to give the corresponding lithium compound.

The process for the preparation of the metallocenes of the formula I is normally carried out in the presence of an inert solvent, e.g. a hydrocarbon or an ether, at temperatures below $-30°$ C., e.g. in the range from $-30°$ to $-100°$ C., preferably from $-60°$ to $-90°$ C., and in an inert gas atmosphere. In one embodiment of the process $LiR^2$ or $LiR^3$ is first prepared by reacting the corresponding halide in ether, as solvent, with butyllithium at a temperature of about $-78°$ C. The appropriate metallocene dihalide is then added to the cooled reaction mixture, the cooling is removed, and the mixture is allowed to warm to room temperature. The reaction mixture is then filtered, optionally after the addition of a solvent, and the metallocene of the formula I is isolated from the solution by precipitation or by evaporating off the solvent.

The compounds so obtained are usually solid crystalline orange-coloured compounds which have high thermal stability and decompose only in their melting range. No decomposition is observed even on exposure to air and water.

The compounds are storage stable and can be handled without inert gas. They are most suitable as very effective photoinitiators for the light-induced polymerisation of ethylenically unsaturated compounds. They are distinguished by very great light-sensitivity and effectiveness over a wide wavelength range from about 200 nm (UV light) to about 600 nm. Further, the titanocenes are also able effectively to initiate the polymerisation under the influence of heat, conveniently in the temperature range from 170° to 240° C. It will be readily understood that the action of light and heat can also be used for the polymerisation, in which case it is possible to carry out the polymerisation, after exposure, at lower temperatures, e.g. in the range from 80° to 150° C.

The present invention also relates to a composition which can be polymerised by irradiation, which composition contains (a) at least one non-volatile monomeric, oligomeric or polymeric compound containing at least one polymerisable ethylenically unsaturated double bond, and (b) at least one titanocene of the formula I

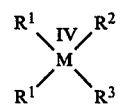    (I)

wherein
  M is the tetravalent titanium atom,
  $R^1$ is each independently unsubstituted or substituted cyclopentadienyl$^\ominus$, indenyl$^\ominus$ or both symbols $R^1$ together denote an unsubstituted or substituted radical of the formula II

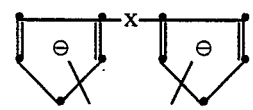    (II)

wherein X is $(CH_2)_n$, in which n is 1, 2 or 3, $C_2$-$C_{12}$alkylidene, cycloalkylidene containing 5 to 7 ring carbon atoms, $SiR_2^4$ or $SnR_2^4$, in which $R^4$ is $C_1$-$C_{12}$alkyl, $C_5$-$C_{12}$cycloalkyl, $C_6$-$C_{16}$aryl or $C_7$-$C_{16}$aralkyl,
  $R^2$ is a 6-membered carbocyclic or 5- or 6-membered heterocyclic aromatic ring which is substituted by fluorine atoms in at least one of the two ortho-positions relative to the metal-carbon bond and which may contain further substituents, or $R^2$ and $R^3$ together are a radical of the formula III

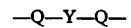    (III)

wherein Q is a carbocyclic or heterocyclic 5- or 6-membered aromatic ring, each of the two bonds is in the ortho-position to the Y group and each meta-position to the Y group is substituted by a fluorine atom, and Q may contain further substituents, and Y is $CH_2$, $C_2$-$C_{12}$alkylidene, cycloalkylidene containing 5 to 7 ring carbon atoms, a direct bond, $NR^4$, O, S, SO, $SO_2$, CO, $SiR_2^4$ or $SnR_2^4$,
  $R^3$ is alkynyl, substituted or unsubstituted phenylalkynyl, $N_3$, CN, $SiR_3^4$ or $SnR_3^4$ or has the meaning of $R^2$,
together with conventional ingredients.

In this composition the metallocenes can have the preferred meanings given above, with the proviso that, for each $R^1$ as unsubstituted $\pi$-cyclopentadienyl, $R^2$ and $R^3$ may also be pentafluorophenyl. A preferred composition is one in which $R^1$ in formula I is unsubstituted or $C_1$-$C_4$alkyl-substituted cyclopentadienyl$^\ominus$ and $R^2$ and $R^3$ are a radical of the formula

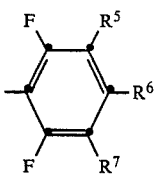

wherein each of $R^5$, $R^6$ and $R^7$ independently is a hydrogen atom, F. Cl, Br, a tertiary amino group, a quaternary ammonium group, a tertiary aminoalkyl group or a quaternary ammoniumalkyl group. The aminoalkyl or ammonium(alkyl) groups are preferably present only once, namely in the para-position as $R^6$. On account of the ease with which they can be obtained, particularly suitable metallocenes are those in which $R^5$, $R^6$ and $R^7$ are fluorine.

The concentration in which the metallocenes are added depends essentially on economic considerations, on their solubilities and on the desired sensitivity. Normally 0.01 to 25% by weight, preferably 0.1 to 20% by weight and, most preferably, 1 to 10% by weight, will be used, based on component (a) and on a binder (c), if present.

Suitable compounds as component (a) are those ethylenically unsaturated monomeric, oligomeric and polymeric compounds which react by photopolymerisation to give higher molecular products and undergo a change in solubility in doing so.

Particularly suitable compounds of this type are e.g. esters and amides of ethylenically unsaturated carboxylic acids and polyols or polyepoxides, and polymers containing ethylenically unsaturated groups in the chain or in side groups, e.g. unsaturated polyesters, polyamides and polyurethanes and copolymers thereof, polybutadiene and polybutadiene copolymers, polymers and copolymers containing acrylic or methacrylic groups in side chains, as well as mixtures of one or more such polymers.

Examples of unsaturated carboxylic acids are acrylic acid, methacrylic acid, crotonic acid, itaconic acid, cinnamic acid, unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenylene, bisphenols such as bisphenol-A, as well as novolaks and resols. Examples of polyepoxides are those based on the above polyols, especially on the aromatic polyols and epichlorohydrin. Suitable alcoholates are also polymers or copolymers containing hydroxyl groups in the polymer chain or in side groups, e.g. polyvinyl alcohol and copolymers or hydroxyalkyl polymethacrylates or copolymers. Further suitable diols are oligoesters containing hydroxyl end groups.

A preferred group of polyols comprises those of the formula $R_n^8(OH)_n$ wherein $R^8$ is an n-valent, preferably di- to octavalent, most preferably di-to hexavalent, aliphatic radical of 2 to 30 carbon atoms, which radical may be interrupted by nitrogen, sulfur and, in particular, oxygen atoms as well as by cycloalkylene, or is cycloalkylene containing 5 or 6 ring carbon atoms.

Examples of polyols are alkylenediols containing preferably 2 to 12 carbon atoms, e.g. ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 100 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol, and sorbitol.

The polyols may be partially or completely esterified with one or with different unsaturated carboxylic acids. In partial esters, the free hydroxyl groups may be modified, e.g. etherified or esterified with other carboxylic acids.

Examples of esters are:
trimethylolpropanetriacrylate, trimethylolethanetriacrylate, trimethylolpropanetrimethacrylate, trimethylolethanetrimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethyacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sorbitol hexaacrylate, pentaerythritol-modified triacrylate, an oligoester acrylate, an oligoester methacrylate, glycerol di- and triacrylate, 1,4-cyclohexane diacrylate, bisacrylates and bismethacrylates of polyethylene glycol having molecular weights of 100 to 1500, or mixtures thereof.

Also suitable as component (a) are the amides of identical or different unsaturated carboxylic acids of aromatic, cycloaliphatic and aliphatic polyamines containing 2 to 6, preferably 2 to 4, amino groups, and 2 to 30, preferably 2 to 18, carbon atoms. Examples of amines are alkylenediamines containing preferably 2 to 22 carbon atoms, e.g. ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetramine, di-($\beta$-aminoethoxy)ethane or di-($\beta$-aminopropoxy)ethane. Further suitable polyamines are polymers and copolymers containing amino groups in the side chain and oligoamides containing amino end groups. Examples are: methylene bisacrylamide, 1,6-hexamethylene bisacrylamide, diethylenetriamine trismethylacrylamide, bis(methacrylamidopropoxy)ethane, $\beta$-methacrylamidoethylmethacrylate, N-[($\beta$-hydroxyethyloxy)ethyl]acrylamide.

Suitable unsaturated polyesters and polyamides are derived e.g. from maleic acid and diols or diamines. The maleic acid can be partially replaced by other dicarboxylic acids. They can be used together with ethylenically unsaturated comonomers, e.g. styrene. The polyesters and polyamides can also be derived from dicarboxylic acids and ethylenically unsaturated diols or diamines, in particular those having a relatively long chain of e.g. 6 to 20 carbon atoms. Examples of polyurethanes are those which are synthesised from saturated or unsaturated diisocyanates and unsaturated or saturated diols.

Polybutadiene and polyisoprene and copolymers thereof are known. Suitable comonomers are e.g. polyolefins such as ethylene, propine, butine, hexene, acrylates and methacrylates, acrylonitrile, styrene or vinyl chloride. Polymers containing acrylate or methacrylate groups in the side chain are also known. They can be e.g. reaction products of novolak epoxy resins with acrylic or methacrylic acid, homo- or copolymers of polyvinyl alcohol or their hydroxyalkyl derivatives which are esterified with acrylic or methacrylic acid, or homo- or copolymers of acrylates or methacrylates which are esterified with hydroxyalkyl acrylates or methacrylates.

The photopolymerisable compounds can be used alone or in any mixtures. It is advantageous to use them in admixture with esters of unsaturated carboxylic acids, especially acrylates or methacrylates of polyols. In another embodiment of the invention, acrylates or methacrylates of polyols are used alone or in mixtures.

It is also possible to add a binder (c). This addition is particularly advantageous if the photopolymerisable compounds are liquid or viscous substances. The amount of the binder (c) can be e.g. from 5 to 95%, preferably 10 to 90%, most preferably 50 to 90%, based on the amount of component (a) and the binder (c) present.

The choice of binder depends on the field of use and on the properties required therefor, for example development in aqueous and organic solvent systems, adhesion to substrates and sensitivity to oxygen.

Suitable binders are e.g. polymers having a molecular weight in the range from about 5000 to 2000,000, preferably from 10,000 to 1,000,000. Examples are: homopolymers and copolymers of acrylates and methacrylates, e.g. copolymers of methylmethacrylate/ethyl acrylate/methacrylic acid, poly(alkylmethacrylates), poly(alkylacrylates), where alkyl=$C_1$-$C_{20}$, cellulose esters and ethers, e.g. cellulose acetate, cellulose acetate butyrate, methyl cellulose, ethyl cellulose, polyvinyl butyral, polyvinyl formal, cyclisèd rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride. Copolymers of vinylidene chloride with acrylonitrile, methylmethacrylate and vinyl acetate, polyvinyl acetate, copoly(ethylene/vinyl acetate), polyamides and polycaprolactams such as polycaprolactam and poly(hexamethyleneadipamide), polyesters such as poly(ethylene glycol terephthalate) and poly(hexamethylene glycol succinate).

The compositions of this invention can contain further ingredients, e.g. inhibitors of thermal polymerisation, pigments, fillers, adhesion promoters, wetting agents and plasticisers. The composit-ions can also be dissolved in a suitable solvent for application.

The compositions of the invention are most suitable for use as coating agents for substrates of all kinds, e.g. wood, paper, ceramics, plastics such as polyesters and cellulose acetate films, and metals such as copper and aluminium to which it is desired to apply a protective layer or a photographic image by photopolymerisation. The invention also relates to the substrates so coated and to a process for applying photographic images to said substrates.

The coated substrates can be produced e.g. by preparing a solution or suspension of the composition.

The choice of solvent and the concentration depends principally on the nature of the composition and on the coating method. The solution is applied uniformly to a substrate by known coating methods, e.g. by immersion, doctor coating, curtain coating, brushing, spraying and reverse roll coating. The add-on (layer thickness) and nature of the substrate (support) depend on the field of application. Suitable substrates for photographic information recording are e.g. sheets made of polyester or cellulose acetate, or plastics coated papers; those for offset formes are specially treated aluminium and copper-coated laminates for making printed circuits. The layer thicknesses for photographic materials and offset formes are about 0.5 to 10 μm, and for printed circuits 1 to about 100 μm.

It is known that the photopolymerisation of acrylates and methacrylates is inhibited by atmospheric oxygen, especially in thin layers. This effect can be diminished by means of known conventional methods, e.g. by applying a covering layer of polyvinyl alcohol or by pre-exposure or preconditioning in an inert gas atmosphere.

After coating, the solvent is removed by drying to leave a layer of light-sensitive polymer on the support. After conventional imagewise exposure of the substrate through a photomask the unexposed areas of the polymer are dissolved out in a developer and the polymer relief, consisting of crosslinked polymer, is exposed. The nature of the developer can be aqueous or organic, depending on the nature and composition of the photopoplymerisable layer. Aqueous carbonate solutions, for example, are suitable for compounds and binders which contain carboxyl groups. Examples of suitable organic developers are chlorinated hydrocarbons such as 1,1,1-trichloroethane, ketones such as cyclohexanone, esters such as butyl acetate and acetoxymethoxyethane, alcohols such as ethyl cellosolve, methyl cellosolve and butanol.

The light-sensitivity of the materials of this invention extends from the UV range (200 nm) to about 600 nm and thus encompasses a very broad range. Accordingly, a large number of the most different types of light sources may be used. Both point sources of light and spatial radiators (arrays of lamps) are suitable. Examples of such light sources are: carbon arc lamps, xenon arc lamps, mercury vapour lamps which may be doped with metal halides (metal halide lamps), fluorescent lamps, argon filament lamps, electronic flash lamps and photographic floodlight lamps. The distance between lamp and the image material of this invention can vary greatly, depending on the intended purpose and the type or strength of lamp, e.g. from 2 cm to 150 cm. Particularly suitable are laser light sources, e.g. argon ion lasers or krypton ion lasers with strong emission lines (Ar lasers) at 457, 476, 488, 514 and 528 nm. In this type of exposure, a photomask in contact with the photopolymer layer is no longer necessary: the guided laser beam writes directly onto the layer. Here the high sensitivity of the materials of the invention is very advantageous and permits high writing speeds at relatively low intensities. Using this method it is possible to produce printed circuits in the electronics industry, lithographic offset printing plates or relief printing plates, as well as photographic image recording materials.

The most important utilities are as discharge resist, galvanoresist and soldering resist for the production of printed circuits and printing plates, for the production of photopolymer printing plates for offset printing, letterpress (relief) printing, as well as for flexographic and silk screen printing as finishing lacquer and for the production of photographic image recording materials, e.g. as disclosed in German Pat. No. 2,651,864 or German Pat. No. 2,202,360.

The invention is illustrated in more detail by the following Examples.

(A) PREPARATION OF STARTING MATERIALS

Synthesis of dimethylaminomethyl p-bromotetrafluorobenzene 10 g (32.5 mmoles) of 1,4-dibromotetrafluorobenzene are dissolved under argon in 100 ml of ether and 100 ml of tetrahydrofuran. The solution is cooled to −78° C. and 21 ml of a 1.6 molar solution of butyllithium in hexane are added. After 15 minutes, 6.08 g (65 mmoles) of N,N-dimethylmethyleneimmonium chloride are added and the mixture is warmed to room temperature. After 1½ hours the mixture is poured into water and extracted with ether. The ethereal extract is dried over $MgSO_4$. The solvent is distilled off, affording as residue a white solid which is distilled at 100° C. under a high vacuum. Yield: 7.8 g (84%) of a colourless product which is solid at room temperature.

(B) PREPARATORY EXAMPLES

Examples 1–28

25 g of bromopentafluorobenzene are dissolved in 750 ml of absolute ether and the solution is cooled, under argon, to −78° C. After addition of 62.5 ml of a 1.6 molar solution of butyllithium in hexane, the mixture is stirred for a further 15 minutes at −78° C., then 12.5 g of $Cp_2TiCl_2$ in powder form are added and the cooling is removed. The mixture warms to room temperature over 2 hours. The orange suspension is concentrated, the residue is suspended in methylene chloride, and the suspension is filtered. The orange product is precipitated by addition of hexane to the orange solution. The precipitate is dried under a high vacuum at room temperature, affording 23.6 g (92%) of $Cp_2Ti(C_6F_5)_2$ in the form of orange crystals which melt at 230° C. with decomposition.

The compounds 2 to 28 listed in the following table are prepared in corresponding manner. Cp=π-cyclopentadienyl.

TABLE

| | | Starting material/Reaction conditions | | |
|---|---|---|---|---|
| Example | Ti-compound | Butyllithium in hexane (1.6 m) | $C_6X_5$—Y | Solutions temperature |
| 1 | $Cp_2TiCl_2$: 12.5 g | 62.5 ml | $C_6F_5Br$: 25 g | 750 ml of abs. ether/−78° |
| 2 | $Cp_2TiCl_2$: 1.245 g | 6.25 ml | 1,4-$Br_2C_6F_4$: 3.08 g | 120 ml of abs. ether/−78° |
| 3 | $Cp_2TiCl_2$: 2.5 g | 13 ml | 1,3-$Br_2C_6F_4$: 6.47 g | 100 ml of abs. ether/−78° |
| 4 | $Cp_2TiCl_2$: 2.5 g | 13 ml | 1-Br-2,3,4,6-$F_4C_6H$ 4.8 g | 160 ml of abs. ether/−78° |
| 5 | $Cp_2TiCl_2$: 2.5 g | 13 ml | 1,3,5-$Cl_3C_6F_3$: 4.92 g | 160 ml of abs. ether/−78° |
| 6 | $Cp_2TiCl_2$: 2.5 g | 13 ml | 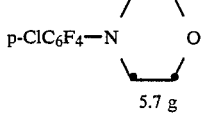 p-$ClC_6F_4$—N⌒O (morpholino) 5.7 g | 80 ml of THF / 80 ml of ether } −78° |
| 7 | $Cp_2TiCl_2$: 2.5 g | 13 ml | 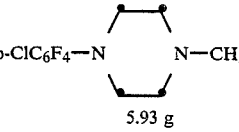 p-$ClC_6F_4$—N⌒N—$CH_3$ 5.93 g | 80 ml of THF / 100 ml of ether } −78° |
| 8 | $(CH_3$—$Cp)_2TiCl_2$: 27.8 g | 125 ml | $C_6F_5Br$: 50 g | 1.2 l of abs. ether/−78° |
| 9 | $(CH_3$—$Cp)_2TiCl_2$: 3.78 g | 13 ml | 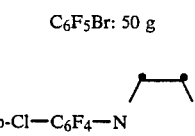 p-Cl—$C_6F_4$—N⌒O 5.7 g | 80 ml of THF / 100 ml of ether } −78° |
| 10 | $(CH_3$—$Cp)_2TiCl_2$: 5.56 g | 27 ml | 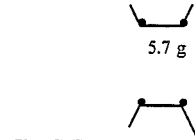 p-Cl—$C_6F_4$—N (pyrrolyl) 11.86 g | 80 ml of THF / 100 ml of ether } −78° |
| 11 | $Cp_2TiCl_2$: 3.375 g | 17 ml | 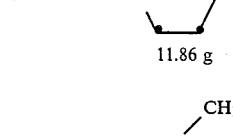 pBr—$C_6F_4$—$CH_2$—N($CH_3$)$_2$ 7.8 g | 200 ml of ether/−78° |

TABLE-continued

| | | Starting material/Reaction conditions | | |
|---|---|---|---|---|
| Example | Ti-compound | Butyllithium in hexane (1.6 m) | C₆X₅—Y | Solutions temperature |
| 12 | Cp₂TiCl₂: 5 g | 27 ml | 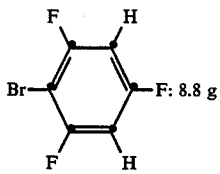 F: 8.8 g | 150 ml of ether abs./−78° |
| 13 | Cp₂TiCl₂: 5 g | 27 ml | 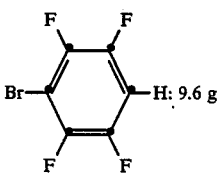 H: 9.6 g | 150 ml of ether abs./−78° |
| 14 | (CH₃—Cp)₂TiCl₂: 5.56 g | 27 ml | 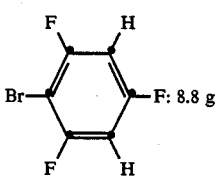 F: 8.8 g | 150 ml of ether abs./−78° |
| 15 | (CH₃—Cp)₂TiCl₂: 5.56 g | 27 ml | 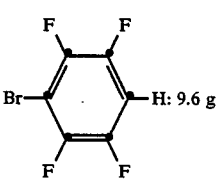 H: 9.6 g | 150 ml of ether abs./−78° |
| 16 | Cp₂TiCl₂: 5 g | 27 ml | 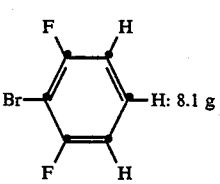 H: 8.1 g | 150 ml of ether abs./−78° |
| 17 | (CH₃—Cp)₂TiCl₂: 5.56 g | 27 ml | 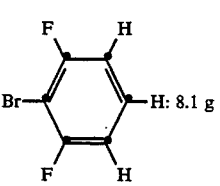 H: 8.1 g | 150 ml of ether abs./−78° |
| 18 | Cp₂TiCl₂: 5 g | 27 ml | 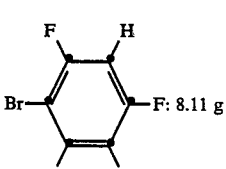 F: 8.11 g | 150 ml of ether abs./−78° |
| 19 | Cp₂TiCl₂: 5 g | 27 ml | 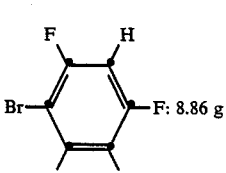 F: 8.86 g | 150 ml of ether abs./−78° |

TABLE-continued

| Example | Ti-compound | Butyllithium in hexane (1.6 m) | $C_6X_5{-}Y$ | Solutions temperature |
|---|---|---|---|---|
| | | Starting material/Reaction conditions | | |
| 20 | $Cp_2TiCl_2$: 5 g | 27 ml | 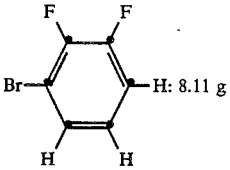 Br—[F,F,H,H]—H: 8.11 g | 150 ml of ether abs./−78° |
| 21 | $Cp_2TiCl_2$: 5 g | 27 ml | 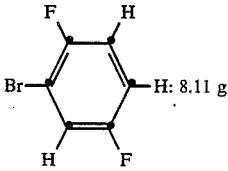 Br—[F,H,H,F]—H: 8.11 g | 150 ml of ether abs./−78° |
| 22 | $(CH_3{-}Cp)_2TiCl_2$: 5.56 g | 27 ml | 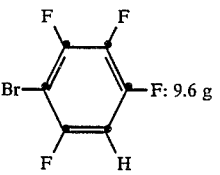 Br—[F,F,F,H]—F: 9.6 g | 150 ml of ether abs./−78° |
| 23 | $Cp_2TiCl_2$: 5 g | 27 ml | 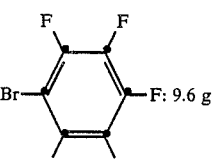 Br—[F,F,H,F]—F: 9.6 g | 150 ml of ether abs./−78° |
| 24 | $(CH_3{-}Cp)_2TiCl_2$: 5.56 g | 27 ml | 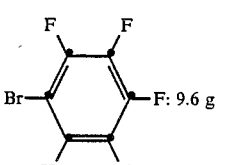 Br—[F,F,H,F]—F: 9.6 g | 150 ml of ether abs./−78° |
| 25 | $Cp_2TiCl_2$: 5 g | 27 ml | 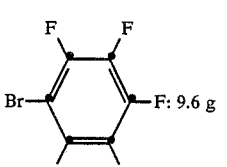 Br—[F,F,H,F]—F: 9.6 g | 150 ml of ether abs./−78° |
| 26 | $(CH_3{-}Cp)_2TiCl_2$: 5.56 g | 27 ml | 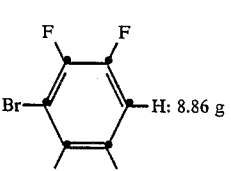 Br—[F,F,F,H]—H: 8.86 g | 150 ml of ether abs./−78° |
| 27 | $\left[\begin{array}{c}H_3C\\ \phantom{H_3C}\diagdown\\ \phantom{xx}CH{-}Cp\\ \phantom{H_3C}\diagup\\ H_3C\end{array}\right]_2 TiCl_2$: 6.12 g | 27 ml | 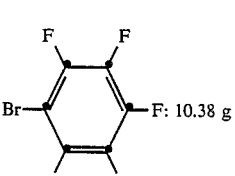 Br—[F,F,F,F]—F: 10.38 g | 150 ml of ether abs./−78° |

TABLE-continued

| Example | Ti-compound | Starting material/Reaction conditions Butyllithium in hexane (1.6 m) | $C_6X_5$—Y | Solutions temperature |
|---|---|---|---|---|
| 28 | $Cp_2TiCl_2$: 5 g | 27 ml | 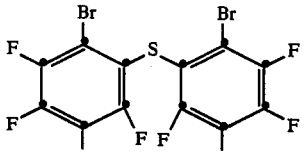<br>10.25 g | 150 ml of ether abs./−78° |

TABLE

Products and Properties

| Example | Formula | Yield | Colour | Decompos. | Properties |
|---|---|---|---|---|---|
| 1 | $Cp_2Ti(C_6F_5)_2$ | 92 | orange | 130° | air-resistant water-resistant light-sensitive |
| 2 | $Cp_2Ti(p\text{-}Br\text{—}C_6F_4)_2$ | 73 | orange | 215° | air-resistant, light-sensitive |
| 3 | $Cp_2Ti(m\text{-}Br\text{—}C_6F_4)_2$ | 85 | orange | 253° | air-resistant, light-sensitive |
| 4 | $Cp_2Ti(m\text{-}H\text{—}C_6F_4)_2$ | 90 | orange | 201° | air-resistant, light-sensitive |
| 5 | $Cp_2Ti(3,5\text{-}Cl_2C_6F_3)_2$ | 76 | orange | 249° | air-resistant, light-sensitive |
| 6 | $Cp_2Ti(p\text{-}C_6F_4\text{—N}\underset{\smile}{\frown}O)_2$ | 74 | red | 228° | air-resistant, light-sensitive |
| 7 | $Cp_2Ti(p\text{-}C_6F_4\text{—N}\underset{\smile}{\frown}N\text{—}CH_3)_2$ | 80 | red | 218° | air-resistant, light-sensitive |
| 8 | $(CH_3\text{—}Cp)_2Ti(C_6F_5)_2$ | 90 | orange | 192° | air-resistant, light-sensitive |
| 9 | $(CH_3\text{—}Cp)_2Ti(p\text{-}C_6F_4\text{—N}\underset{\smile}{\frown}O)_2$ | 85 | red | 212° | air-resistant, light-sensitive |
| 10 | $(CH_3\text{—}Cp)_2Ti(p\text{-}C_6F_4\text{—N}\underset{\smile}{\frown}N\text{—}CH_3)_2$ | 88 | red | 190° | air-resistant, light-sensitive |
| 11 | $Cp_2Ti[p\text{-}C_6F_4\text{—}CH_2\text{—}N(CH_3)_2]_2$ | 93 | orange | 203° | air-resistant, light-sensitive |
| 12 | $Cp_2Ti\text{—}[2,5\text{-}F_2\text{-}3,6\text{-}H_2\text{-}C_6]_2$ | 77 | orange | 208° | air-resistant, light-sensitive |

TABLE-continued

Products and Properties

| Example | Formula | Yield | Colour | Decompos. | Properties |
|---|---|---|---|---|---|
| 13 | Cp₂Ti—[C₆F₄H]₂ (2,3,5,6-tetrafluorophenyl) | 94 | orange | 218° | air-resistant, light-sensitive |
| 14 | (CH₃—Cp)₂Ti—[C₆F₂H₂F]₂ | 78 | orange | 165° | air-resistant, light-sensitive |
| 15 | (CH₃—Cp)₂Ti—[C₆F₄H]₂ | 43 | orange | 192° | air-resistant, light-sensitive |
| 16 | Cp₂Ti—[C₆F₂H₃]₂ | 81 | orange | 205° | air-resistant, light-sensitive |
| 17 | (CH₃—Cp)₂Ti—[C₆F₂H₃]₂ | 78 | orange | 190° | air-resistant, light-sensitive |
| 18 | Cp₂Ti—[C₆F₂H₃]₂ | 75 | yellow orange | 167° | air-resistant, light-sensitive |
| 19 | Cp₂Ti—[C₆F₂H₃]₂ | 72 | yellow orange | 160° | air-resistant, light-sensitive |

TABLE-continued

| Example | Formula | Yield | Colour | Decompos. | Properties |
|---|---|---|---|---|---|
| 20 | [Cp₂Ti—C₆F₂H₃]₂ (2,3-F₂) | 70 | yellow orange | 160° | air-resistant, light-sensitive |
| 21 | [Cp₂Ti—C₆F₂H₃]₂ (2,5-F₂) | 85 | yellow orange | 170° | air-resistant, light-sensitive |
| 22 | [(CH₃—Cp)₂Ti—C₆F₄H]₂ | 85 | orange | 167° | air-resistant, light-sensitive |
| 23 | [Cp₂Ti—C₆F₄H]₂ | 90 | orange | 195° | air-resistant, light-sensitive |
| 24 | [Cp₂Ti—C₆F₄H]₂ | 80 | orange | 150° | air-resistant, light-sensitive |
| 25 | [Cp₂Ti—C₆F₃H₂]₂ | 90 | orange | 217° | air-resistant, light-sensitive |
| 26 | [(CH₃—Cp)₂Ti—C₆F₃H₂]₂ | 82 | orange | 150° | air-resistant, light-sensitive |
| 27 | $\left[\begin{array}{c}H_3C\\ \phantom{H_3C}CHCp\\ H_3C\end{array}\right]_2 Ti(C_6F_5)_2$ | 80 | orange | 229° | air-resistant, light-sensitive |

TABLE-continued

| Example | Formula | Yield | Colour | Decompos. | Properties |
|---|---|---|---|---|---|
| 28 | 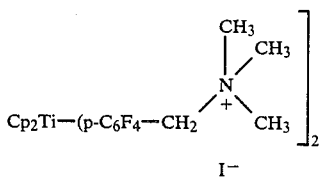 | 20 | orange | 229° | air-resistant, light-sensitive |

Example 29

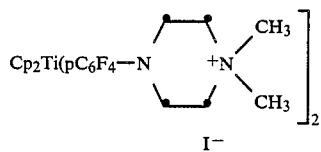

1.35 g of

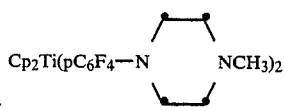

are dissolved in 30 ml of CH₃CN, then 0.5 ml of methyl iodide is added to the solution and the mixture is stirred for 1 hour at room temperature. The orange solution is concentrated and the crude product is recrystallised from methanol, affording 1.72 g (90%) of orange crystals which melt at 208° C. with decomposition.

Example 30

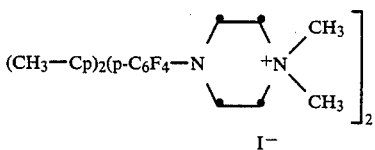

12 g of

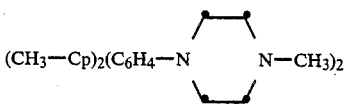

are dissolved in 70 ml of CH$_2$Cl$_2$. The solution is diluted with 200 ml of CH$_3$CN and 5 ml of methyl iodide are added. After 1 hour the orange solution is concentrated and the crude product is recrystallised from methanol/ether, affording 15 g (90%) of orange crystals which melt at 211° C. with decomposition.

Example 31

$$Cp_2Ti—(p\text{-}C_6F_4—CH_2—\overset{+}{N}(CH_3)_3)_2 \quad I^-$$

4.8 g of Cp$_2$Ti—(p—C$_6$F$_4$—CH$_2$N(CH$_2$)$_2$ are dissolved in 45 ml of methylene chloride. The solution is diluted with 150 ml of acetonitrile and 2.03 ml of methyl iodide are added. After 1 hour the orange suspension is filtered, affording 5.2 g (73%) of orange crystals which melt at 262° C. with decomposition. Another 1.5 g (21%) of product can be isolated from the mother liquor.

(C) Use Examples

Examples 32–49

All operations are carried out under red light.

A coating solution of the following composition is prepared:

| (MEK/MCS = mixture of methyl ethyl ketone/methyl cellosolve,1:1 v/v/) | |
|---|---|
| cellulose acetate butyrate (10% solution in MEK/MCS) | 10.00 g |
| pentaerythritol triacrylate (10% solution in MEK/MCS) | 10.00 g |
| sensitiser | 0.100 g |
| red pigment composition (Mikrolithrot 241-GP60) | 0.100 g |
| di-tert-butyl p-cresol (DBPC) | 0.002 g |

The components are mixed and then stirred until dissolved. A pretreated aluminium sheet (offset plate substrate) is coated with the solution to a wet film thickness of 40 μm using a wire applicator and the coating is dried for 3 minutes at 80° C. To this dry light-sensitive layer is then applied a polyvinyl alcohol protective layer prepared from a solution of the following composition:

| polyvinyl alcohol (Mowiol 4-88) | 10.00 g |
|---|---|
| Triton X-100 | 0.100 g |
| deionised water | 90.00 g |

This protective layer is applied to a wet film thickness of 40 μm and dried for 5 minutes at 80° C.

The light-sensitive material is exposed in contact with a test negative having a neutral grey wedge with density increments of OD=0.15 (Stouffer wedge). The exposure device employed is a copying machine (Océ Helioprint 36) with a 1,000 W metal halide lamp at a distance of 53 cm. The exposure time is controlled by a photocell (1 impulse=approx. 1 second).

Following exposure, the polyvinyl alcohol protective layer is removed by rinsing with water for 1 minute. The coloured relief image is developed by immersing the light-sensitive layer in an agitated 1:1 solution of MEK/MCS at room temperature for 1½ minutes, rinsing it with a fresh 1:1 solution of MEK/MCS and drying it in the air. Sensitivity is determined by counting the number of reproduced wedge steps. The results are reported in the following table.

TABLE

| Example | Sensitiser | Number of reproduced wedge steps at an exposure time of (number of impulses) | | | |
|---|---|---|---|---|---|
| | | 1 I | 5 I | 10 I | 15 I |
| 32 | 1 | 7 | 12 | 14 | 15 |
| 33 | 8 | 6 | 11 | 13 | 14 |
| 34 | 2 | 7 | 12 | 14 | 15 |
| 35 | 5 | 6 | 11 | 12 | 13 |
| 36 | 4 | 7 | 12 | — | 16 |
| 37 | 6 | 6 | 11 | — | 15 |
| 38 | 7 | 1-2 | 5 | — | 10 |

Examples 39 and 40

These Examples show the influence of the initiator concentration on the sensitivity. The coating solution of Example 32 is used with different amounts of initiator I and the procedure of Example 32 is repeated.

| Example 28: compound 1 | 0.020 g |
|---|---|
| Example 32: compound 1 | 0.100 g |
| Example 29: compound 1 | 0.200 g |

The results are reported in the following table:

TABLE

| Example | Sensitiser | Exposure time (number of impulses) | | | |
|---|---|---|---|---|---|
| | | 1 I | 5 I | 10 I | 15 I |
| 39 | 1%(**) | 3(*) | 8 | 11 | 12 |
| 32 | 5% | 7 | 12 | 14 | 15 |
| 40 | 10% | 9 | 14 | 15 | 17 |

(*)number of reproduced wedge steps (33) percentage amount, based on binder polymer + oligomeric acrylate

Example 41

Exposure with Visible Light

The light-sensitive material of Example 21 are used. The exposure device is a xenon lamp with CG 475 cut-off filter (Jena-Schott) at a distance of 108 cm. This filter absorbs all radiation below 485 nm. Development and evaluation are made in accordance with Example 32. The results are reported in the following table.

TABLE

| Example | Sensitiser | Exposure time in minutes | | | | |
|---|---|---|---|---|---|---|
| | | 1 | 2 | 3 | 4 | 5 min |
| 41 | 1 (5%) | 1(*) | 3 | 4 | 5 | 6 |

(*)number of reproduced wedge steps

Example 42

Exposure with Visible Laser Light (514 nm)

The light-sensitive material of Example 21 is used. The light source is the beam of an argon ion laser with a diameter of about 1 mm and a line frequency of 514 nm. The strength can be variably adjusted with an absorption filter. The light-sensitive material is secured to a rotating circular disc and conveyed past the fixed laser beam at known rotational speed. The samples so exposed with a circular line pattern are developed in accordance with Example 32. The circle is visibly reproduced at a laser strength of 0.5 watt and a tracing speed of 0.35 m/sec.

Example 43

Thermal stability

The light-sensitive material of Example 32 is used. It is heated in an oven for 16 hours at 80° C. in air and then exposed and developed as in Example 32. The material can also be readily developed after this thermal treatment.

Example 44

The following coating solution is prepared:

| copolymer of methylmethacrylate/ethyl acrylate/ methacrylic acid in the percentage weight ratio of 60:25:15 (10% solution in MEK/MCS) | 10.00 g |
|---|---|
| pentaerythritol triacrylate (10% solution in MEK/MCS) | |
| initiator 1 | 0.100 g |
| red pigment composition (Mikrolith 241-GB60) | 0.100 g |
| di-tert-butyl p-cresol | 0.002 g |

The solution is coated on aluminium as described in Example 32 and then a polyvinyl alcohol protective coating is applied. After an exposure time of 15 impulses with the copying machine used in Example 32, the light-sensitive material is developed for 30 seconds at room temperature in agitated 1% Na$_2$CO$_3$ solution, rinsed for 15 seconds with water and dried. 10 wedge steps are reproduced.

Example 45

The following coating solution is prepared:

| copolymer of methylmethacrylate/ethyl acrylate/ methacrylic acid in the percentage weight ratio 60:25:15 | 5.100 g |
|---|---|
| triethylene glycol dimethacrylate | 0.900 g |
| sensitiser 1 | 0.300 g |
| dye (Orasol B) | 0.012 g |
| di-tert-butyl p-cresol | 0.030 g |
| methyl cellosolve | 14.00 g |

The solution is coated with a wire applicator to a wet film thickness of 100 μm on a copper-coated laminate which is used for making printed circuit boards, and dried for 25 minutes at 80° C. The photopolymer layer thickness is about 30 μm. The board is exposed for 30 impulses in the copying machine used in Example 32 through a test negative and developed by immersion in agitated 1% Na$_2$CO$_3$ solution. The conductor leads can then be reinforced on this board by galvanic deposition of copper.

Example 46

1.0 g of polybutadiene ($\overline{M}_w=0.67\cdot10^6$, $\overline{M}_w/\overline{M}_n=8.7$, 97% of cis-1,4-, 2% of trans-1,4-, 1% of 1,2-vinyl structures) and 50 mg of $(C_5H_5)_2Ti(C_6F_5)_2$ are dissolved in 9.45 g of toluene and the solutions is coated on a copper-coated printed circuit board with a 50 μm doctor blade under red light. The coating is dried for 3 minutes at 80° C. and exposed through a Stouffer step wedge (21 step sensitivity guide) with a 5000 watt high-pressure burner at a distance of 70 cm. The unexposed areas are washed off for 2 minutes with toluene. The results are reported in the following table.

TABLE

| Exposure time (minutes) | Number of reproduced wedge steps |
|---|---|
| 2 | 1 |
| 3 | 3 |
| 4 | 5 |

Example 47

1.0 g of an unsaturated polyamide with the repeating unit

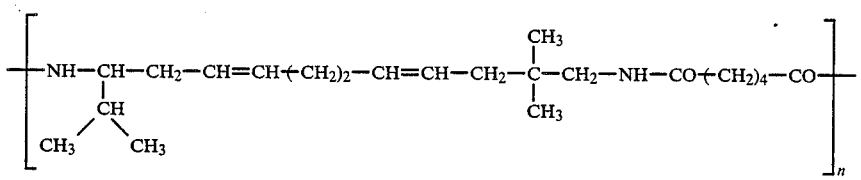

(intrinsic viscosity=0.88 dl/g in an 0.5% solution of m-cresol at 25° C.) and 50 mg of $(C_5H_5)_2Ti(C_6F_5)_2$ are dissolved in 9.45 g of chloroform and further processed as in Example 35.

The coating is exposed for 10 minutes and the non-exposed areas are washed off with chloroform. The contours of the copy of the photographic mask appear.

Example 48

5.0 g of Setarol 3606 MV (a 41% solution in styrene of a polyester of 100 parts by weight of propylene glycol, 72 parts by weight of maleic anhydride and 54 parts by weight of phthalic anhydride, with a viscosity of 1000 mPa s at 20° C., available from Synthese B.V.) and 100 mg of $(C_5H_5)_2Ti(C_6F_5)_2$ are mixed together. The solution is coated on a copper-coated printed circuit board using a 4 μm doctor blade and the coating is exposed through a Stouffer photo-graphic step wedge (21 step sensitivity guide) with a 2000 watt high-pressure lamp from a distance of 70 cm. The unexposed areas are washed off with acetone. The results are reported in the following table.

TABLE

| Exposure time (sec.) | Number of reproduced wedge steps |
|---|---|
| 2 | 2 |
| 3 | 3 |
| 5 | 5 |

Example 49

0.5 g of a polyester of maleic anhydride and cyclohexane dimethanol (Tg=40° C., intrinsic viscosity=0.92 dl/g in a 0.5% solution of m-cresol) and 25 mg of $Cp_2Ti(C_6F_5)_2$ are dissolved in 9.5 g of chloroform and this solution is coated on a copper printed circuit board with a 50 μm doctor blade under red light. The coating is dried for 3 minutes at 80° C. and exposed through a Stouffer step wedge (21 step sensitivity guide) with a 5000 watt high-pressure burner (MO 23 or MO 33 Sylvania ®) from a distance of 70 cm. The non-exposed areas are washed off for 30 seconds with dimethylformamide. The results are reported in the following table.

TABLE

| Exposure time (sec.) | | Number of reproduced wedge steps |
|---|---|---|
| MO 23 | MO 35 | |
|  | 60 | 3 |
|  | 120 | 5 |
| 60 |  | 14 |

Examples 50-64

The following coating solution is prepared:
50 parts by weight of the copolymer of Example 44 (10% solution in MEK/MCS)
50 parts by weight of pentaerythritol triacrylate (10% solution in MEK/MCS)
5 parts by weight of titanocene initiator
0.1 part by weight of di-tert-butyl p-cresol The solution is coated on aluminium as described in Example 32, dried, and then the dried coating is provided with a protective polyvinyl alcohol coating (about 3 g/m²). The light-sensitive coating is then exposed with 10 impulses through a Stouffer step wedge and developed for 60 seconds at 20° C. with a 1% aqueous solution of $Na_2CO_3$. The image is visualised by subsequently colouring with a 1% aqueous solution of the dye, Rhodamine B ®, at pH 7 for 30 seconds at 20° C.

The initiators employed and the number of reproduced steps are listed in the following table.

TABLE

| Example | Sensitiser | Number of reproduced steps |
|---|---|---|
| 50 | $Cp_2Ti(C_6F_5)_2$ | 14 |
| 51 | $(CH_3Cp)_2Ti(C_6F_5)_2$ | 11 |
| 52 | $(Cp)_2Ti(p-BrC_6F_4)_2$ | 10 |
| 53 | $(Cp)_2Ti(m-HC_6F_4)_2$ | 14 |
| 54 | 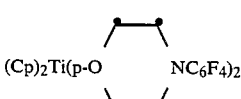 (Cp)$_2$Ti(p-O—NC$_6$F$_4$)$_2$ | 11 |
| 55 | 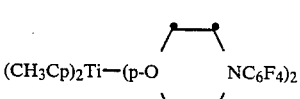 (CH$_3$Cp)$_2$Ti—(p-O—NC$_6$F$_4$)$_2$ | 11 |
| 56 | $(Cp)_2Ti(3,5-H_2C_6F_3)_2$ | 13 |
| 57 | $(CH_3Cp)_2Ti(3,5-H_2C_6F_3)_2$ | 12 |

TABLE-continued

| Example | Sensitiser | Number of reproduced steps |
|---|---|---|
| 58 | $(Cp)_2Ti(2,6-F_2C_6H_3)_2$ | 15 |
| 59 | $(CH_3Cp)_2Ti(2,6-F_2C_6H_3)_2$ | 13 |
| 60 | $(Cp)_2Ti(o-HC_6F_4)_2$ | 11 |
| 61 | $(CH_3Cp)_2Ti(o-HC_6F_4)_2$ | 12 |
| 62 | $(Cp)_2Ti(2,3,6-F_3C_6H_2)_2$ | 14 |
| 63 | $(CH_3Cp)_2Ti(2,3,6-F_3C_6H_2)_2$ | 11 |
| 64 | $[(CH_3)_2CHCp]_2Ti(C_6F_5)_2$ | 11 |

Example 65

Determination of Sensitivity at 488 nm and 515 nm Storage Light

The following coating solution is prepared under red light:

| | |
|---|---|
| copolymer of methylmethacrylate/ethyl methacrylate/methacrylic acid in the percentage weight ratio 65:25:15 (40% solution in MEK) | 2.50 g |
| pentaerythritol triacrylate (40% solution in MEK) | 2.50 g |
| sensitiser 1 (1 g of sensitiser in 100 ml of ethyl glycol acetate) | 10.00 g |
| Oralsolrosa 5 BLG ® (1 g of dye in 100 ml of ethyl glycol) | 2.00 ml |
| di-tert-butyl p-cresol (1 g in 100 ml of ethyl glycol acetate) | 0.20 ml |
| ethyl glycol acetate | 2.00 ml |

This solution is spin-coated on aluminium plates and the coated plates are dried for 5 minutes at 80° C. Add-on=1.15 g/m². A polyvinyl alcohol protective layer is then applied. Add-on=about 3.0 g/m². Exposure is then effected with an expanded argon laser beam (I=1 mW/cm², coherent 90-5) through a diaphragm (diameter 1 cm). The exposure times are: 0.2, 0.4, 0.6, 0.8, 1 and 2 sec. The material is slightly advanced after each exposure, so that a series of exposed circular areas results. The exposed material is developed as follows:

| | |
|---|---|
| rinsing with mains water | 1 min. |
| development in a 1% solution of $Na_2CO_3$ at 20° C. | 1 min. |
| rinsing with mains water | 15 sec. |

The last, still visible circular area indicates the minimum exposure energy $E_{min.}$ required.

Results (A) Laser light of 488 nm: $E^{488}_{min.}=0.4-0.6$ mJ/cm².

(B) Laser light of 514.5 nm: $E^{514}_{min}=0.8-1.0$ mJ/cm².

Example 66

The following components are used:
Polyamide acid ($M_w$=14,000) containing repeating structural units of the formula

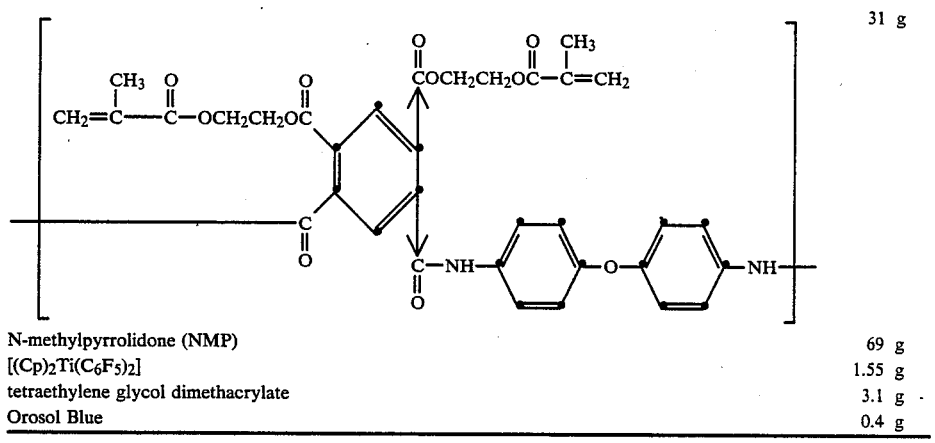

31 g

| | |
|---|---|
| N-methylpyrrolidone (NMP) | 69 g |
| $[(Cp)_2Ti(C_6F_5)_2]$ | 1.55 g |
| tetraethylene glycol dimethacrylate | 3.1 g |
| Orosol Blue | 0.4 g |

The components are mixed and dissolved and the solution is applied with a blade coating machine to aluminium substrates (thickness of the undried layer about 12 μm). After the layer has been dried in a circulating draught oven at 70° C. for 10 minutes, exposure is made with a mercury high pressure lamp. Development is carried out for 22 seconds in an immersion bath of toluene and 4-butyrolactone in the ratio 1:1 at 23° C. At a lamp strength of of 37.5 mW/cm² and a sub-strate temperature close to 23° C., an exposure time of only 1 sec. is required to produce 2 to 3 steps with a Stouffer neutral grey wedge.

What is claimed is:

1. A photopolymerizable composition, which can be polymerized by irradiation, which comprises
    (a) at least one ethylenically unsaturated monomeric, oligomeric or polymeric compound which reacts by photopolymerization to give higher molecular weight products and which undergoes a change in solubility in doing so, and
    (b) 0.01 to 25% by weight, based on component (a), of at least one titanocene of formula I as photoinitiator

wherein
M is a tetravalent titanium atom, $R^1$ is each independently cyclopentadienyl$^\ominus$, indenyl$^\ominus$ or both symbols $R^1$ together denote a radical of the formula II

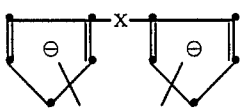 (II)

wherein X is $(CH_2)n'$ in which n is 1, 2 or 3, $C_2$–$C_{12}$alkylidene, cycloalkylidene containing 5 to 7 ring carbon atoms, or $R^1$ is said cyclopentadienyl, idenyl or radical of formula II which is substituted by alkyl, by alkenyl or by alkoxy of up to 18 carbon atoms; by cycloalkyl or by cycloalkenyl of 5 to 8 ring carbon atoms; by aryl of 6 to 16 carbon atoms; by aralkyl of 7 to 16 carbon atoms; by halogen; by amino or by aminoalkyl of up to 12 carbon atoms wherein the amino group is unsubstituted or substituted by alkyl of up to 12 carbon atoms or quaternized with an alkyl halide of up to 12 carbon atoms, $R^2$ is a 6-membered carbocyclic or 5- or 6-membered heterocyclic aromatic ring which is substituted by fluorine atoms in at least one of the two ortho-positions relative to the metal-carbon bond, or $R^2$ and $R^3$ together are a radical of the formula III

—Q—Y—Q— (III)

wherein Q is a carbocyclic or heterocyclic 5- or 6-membered aromatic ring and each of the two bonds is in the ortho-position to the Y group and each meta-position to the Y group is substituted by a fluorine atom; or wherein said aromatic ring of $R^2$ or Q, respectively, is further substituted by alkyl or by alkoxy of 1 to 18 carbon atoms, by cycloalkyl of 5 to 6 ring carbon atoms; by aryl of 6 to 16 carbon atoms; by aralkyl of 7 to 16 carbon atoms; by hydroxyl; by carboxyl; by halogen; by amino which is unsubstituted or substituted by alkyl of 1 to 2 carbon atoms or quaternized with an alkyl halide of up to 12 carbon atoms; by pyrrolidino, by piperidino, by piperazino, by morpholino or by N-methylpiperazino; by alkoxycarbonyl of 1 to 18 carbon atoms in the alkoxy moiety; by aminocarbonyl containing one or two $C_1$–$C_{12}$alkyl groups on the amino moiety; or by aminocarbonyl containing a pyrrolidino, piperidino, piperazino, N-methylpiperazino or morpholino group; or by aminoalkyl of up to 6 carbon aboms wherein the amino group is unsubstituted or substituted by alkyl of up to 12 carbon atoms or quaternized with an alkyl halide of up to 12 carbon atoms, and Y is $CH_2$, $C_2$–$C_{12}$alkylidene, cycloalklidene containing 5 to 7 ring carbon atoms, a direct bond, $NR_4$, O, S, SO, $SO_2$, or CO in which $R^4$ is $C_1$–$C_{12}$alkyl, $C_5$–$C_{12}$cycloalkyl, $C_6$–$C_{16}$aryl or $C_7$–$C_{16}$aralkyl, and $R^3$ has the meaning of $R^2$.

2. A composition according to claim 1, wherein the compound (a) is selected from the group consisting of the esters and amides of unsaturated carboxylic acids, unsaturated polyesters, polyamides and polyurethanes, polybutadiene and polybutadiene copolymers, polyisoprene and polyisoprene copolymers.

3. A composition according to claim 1, wherein the compound (a) is an acrylate or methacrylate of an organic polyol.

4. A composition according to claim 1, wherein $R^1$ in formula I is unsubstituted or $C_1$–$C_4$alkyl-substituted cyclopentadienyl$^\ominus$ and $R^2$ and $R^3$ are a radical of the formula

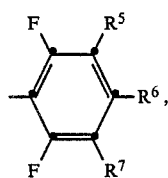

wherein each of $R^5$, $R^6$ and $R^7$ independently is a hydrogen atom, F, Cl, Br, a tertiary amino group, a quaternary ammonium group, a tertiary aminoalkyl group or a quaternary ammonium group.

5. A composition according to claim 4, wherein $R^5$, $R^6$ and $R^7$ are fluorine.

6. A coated substrate which contains a composition according to claim 1 a photopolymerizable layer.

* * * * *